US005545231A

United States Patent [19]

Houser

[11] Patent Number: 5,545,231
[45] Date of Patent: Aug. 13, 1996

[54] ANGULAR ADJUSTMENT SYSTEM FOR PYLON/PROSTHETIC FOOT INTERFACE

[75] Inventor: Guy M. Houser, Bainbridge Island, Wash.

[73] Assignee: Model & Instrument Development Corporation, Poulsbo, Wash.

[21] Appl. No.: 321,254

[22] Filed: Oct. 11, 1994

[51] Int. Cl.[6] .................................................. A61F 2/66
[52] U.S. Cl. ............................................. 623/38; 623/48
[58] Field of Search ............................. 623/38, 47, 48, 623/53

[56] References Cited

U.S. PATENT DOCUMENTS

| 3,206,235 | 9/1965 | Albinson et al. | 623/38 |
| 3,414,908 | 12/1968 | Waggott et al. | 623/38 |
| 4,461,045 | 6/1984 | Shorter et al. | 623/47 |

FOREIGN PATENT DOCUMENTS

| 1261716 | 1/1972 | United Kingdom | 623/38 |
| 2127698 | 4/1984 | United Kingdom | 623/38 |
| 9317640 | 9/1993 | WIPO | 623/38 |

Primary Examiner—David H. Willse
Assistant Examiner—Bruce E. Snow
Attorney, Agent, or Firm—Seed and Berry LLP

[57] ABSTRACT

A system for adjusting the angle between a pylon and prosthetic foot in either or both of the medial/lateral plane or the anterior/posterior plane by placing at least one wedge between the pylon and the prosthetic foot. A barrel nut mounted in the lower end of a prosthetic pylon mates with a bolt extending from the prosthetic foot to secure the foot to the pylon. The angle of the barrel nut is adjusted in the anterior/posterior plane so that a threaded bore of the barrel nut is aligned with the bolt as its angle varies according to the angle of the wedge positioned between the pylon and prosthetic foot. For the same reason, the position of the barrel nut in the medial/lateral plane may be adjusted.

7 Claims, 6 Drawing Sheets

ANGULAR ADJUSTMENT SYSTEM FOR PYLON/PROSTHETIC FOOT INTERFACE

FIELD OF THE INVENTION

This invention relates to prosthetic devices and, more particularly, to a system for adjusting the angle between a prosthetic pylon and a prosthetic foot to accommodate variations in the angle of inclination of the pylon.

BACKGROUND OF THE INVENTION

Prosthetic devices have enabled amputees to regain mobility impaired by loss of a limb, to participate again in activities enjoyed before such a loss, and to participate in new activities for the first time. Moreover, with amputees fully engaging in today's active lifestyles, amputees are participating in events such as marathons, basketball, and free-style downhill skiing.

The stump of an amputee's limb is typically placed in a socket having an inter contour that conforms to the shape of the stump. A fitting mounted on the lower end of the socket is then attached to the upper end of an elongated prosthetic pylon. Finally, a prosthetic foot is bolted to the lower end of the pylon. The pylon thus serves as the structural member used to interconnect the limb socket and the prosthetic foot.

It is desirable for the bottom of the prosthetic foot to be substantially horizontal so that a major portion of the foot's bottom surface contacts the ground or floor during walking or running. However, as is sometimes the case, if the pylon is canted to the side in the medial/lateral plane or to the front or back in the anterior/posterior plane, a relatively small portion of the bottom surface of the prosthetic foot will make contact with the ground or floor. This makes walking or running awkward for the amputee because it applies an unbalanced load to the amputee's limb.

There has heretofore not been any satisfactory means for effectively dealing with pylons that are not substantially vertical in their normal standing position. While various angular adjusting mechanisms could be used as part of the pylon or prosthetic foot themselves, a satisfactory means to adjust the angle between an existing pylon and a prosthetic foot that has a pre-existing bolt hole and attachment structure has been needed.

SUMMARY OF THE INVENTION

The primary object of the present invention is to provide a system for adjusting the angle between a prosthetic pylon and a prosthetic foot.

It is another object of the invention to provide an angular adjustment system for a pylon/prosthetic foot interface that is relatively light in weight.

It is still another object of the invention to provide an angular adjustment system for a pylon/prosthetic foot interface that does not appreciably alter the flexure characteristics of the pylon.

It is another object of the invention to provide an angular adjustment system for a pylon/prosthetic foot interface that may use existing pylon and prosthetic foot technology.

These and other objects of the invention are provided by a system for adjusting the angle between an elongated pylon and a prosthetic foot having a bottom, a pylon attachment surface that is generally parallel to the bottom, and a bolt hole extending through the attachment surface. The angular adjustment system includes a wedge positioned between the attachment surface and the pylon. The wedge has a bolt hole extending therethrough, and the wedge is positioned so that its bolt hole is in alignment with the bolt hole through the attachment surface. A threaded fastener is mounted in the pylon adjacent the lower end thereof, and is adapted to mate with threads of the bolt extending from the prosthetic foot. The threaded fastener is mounted in the pylon at an angle that corresponds to the wedge angle and at a radial position that causes the axis of the threaded fastener to intersect the bolt hole through the pylon attachment surface. The threaded fastener is preferably movably mounted in the pylon so that the fastener may be moved to a variety of angles and radial positions to accommodate wedges having a corresponding variety of wedge angles. For example, the threaded fastener may be angularly and radially movable in the anterior-posterior plane, it may be angularly and radially movable in the medial-lateral plane, and it may be angularly and radially movable in both planes.

The threaded fastener preferably comprises a nut mounted in the pylon, and adjusting means are provided for allowing the nut to move to a variety of angles and radial positions. Although a variety of configurations can be used, the nut may be a cylindrical barrel nut member having a threaded bore extending therethrough to receive the bolt, and a pair of axles extending from opposite end faces of the barrel nut member. The barrel nut member may be rotatably supported by a pair of cylindrical bearings mounted in the pylon. The bearings slidably engage each of the axles with the centers of the bearings being radially offset in opposite directions from the axis of the cylindrical barrel nut member. As a result, rotation of the barrel nut member in the bearings varies the angle of the axis of the threaded bore in the anterior/posterior plane. The width of the bearings are preferably different from each other so that the location of the threaded bore in the medial/lateral plane can be varied between two positions to accommodate different wedges by altering which of the two bearings are located at one side of the pylon.

The wedges used in the inventive adjusting system preferably include an alignment structure that interfits with an alignment structure of the prosthetic foot to restrain movement of the prosthetic foot relative to the wedge in at least one direction.

DETAILED DESCRIPTION OF THE INVENTION

Figure 1:
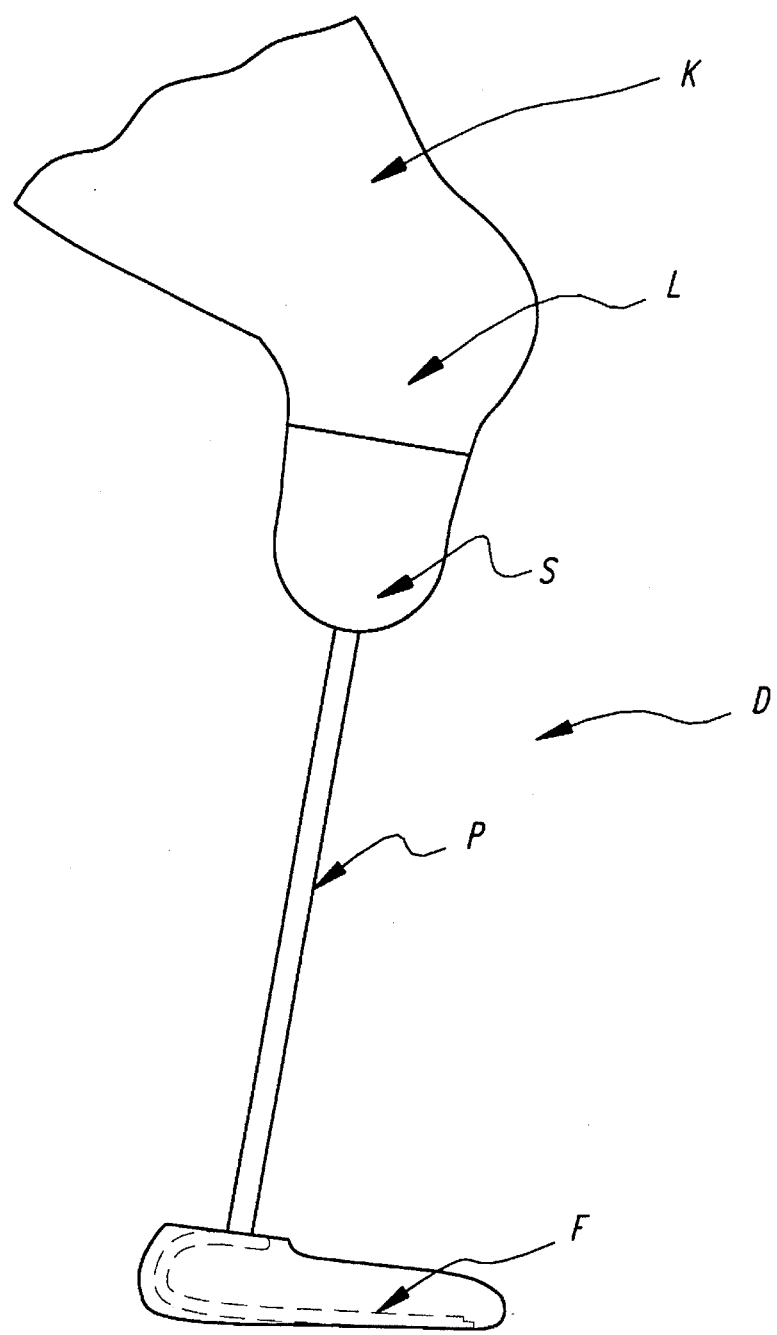
FIG. 1 is a side elevational view of a typical prosthetic pylon and foot attached to the limb stump of an amputee.

As shown in FIG. 1, a typical prosthetic device D consists of a socket S, a pylon P, and a prosthetic foot F. The socket S fits over the lower end of the stump of a limb L extending from a knee K. The pylon P attaches to a fitting on the lower end of the socket S, and the prosthetic foot F is attached to the lower end of the pylon P with a bolt B that threadingly engages an axial bore formed in the pylon P. As the amputee walks or runs on the prosthetic device D, axial forces and torque are imparted to the pylon P between the prosthetic foot F and the socket S. It is generally desirable for the pylon P to flex to some degree when axial forces and torque are applied to the pylon P so that the pylon P absorbs forces that might otherwise be uncomfortably large if applied to the socket S.

Figure 2:
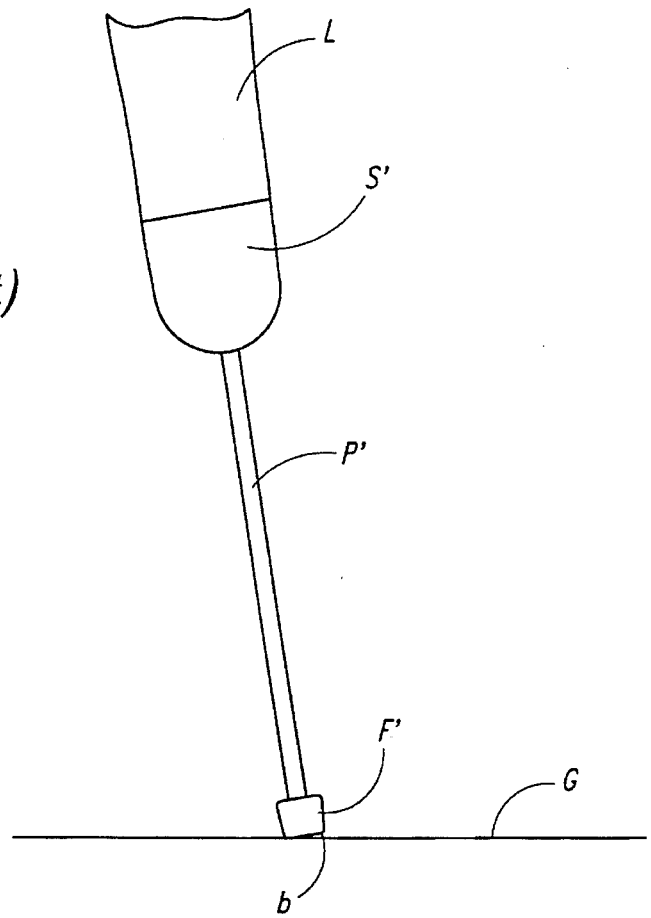
FIG. 2 is a side elevational view of a typical prosthetic pylon and foot supported on a horizontal surface in which the pylon angles outwardly in the lateral direction.

The prior art pylon and prosthetic foot of FIG. 1 is shown in FIG. 2 in a situation in which a pylon P' extending from a socket S' is canted to one side in the medial/lateral plane. As a result, most of the bottom surface b of the prosthetic foot F' does not contact the ground G on which the amputee is walking or running. In addition to being unsafe because of the relatively small amount of contact between the foot F' and ground G, the uneven contact between the foot F' and ground G produces a torque in the pylon P' that induces torque and lateral forces in the socket S'. These torque and lateral forces are uncomfortable to the amputee. A similar situation, although less severe, is created by the pylon P' being canted in the anterior/posterior plane.

Figure 3:
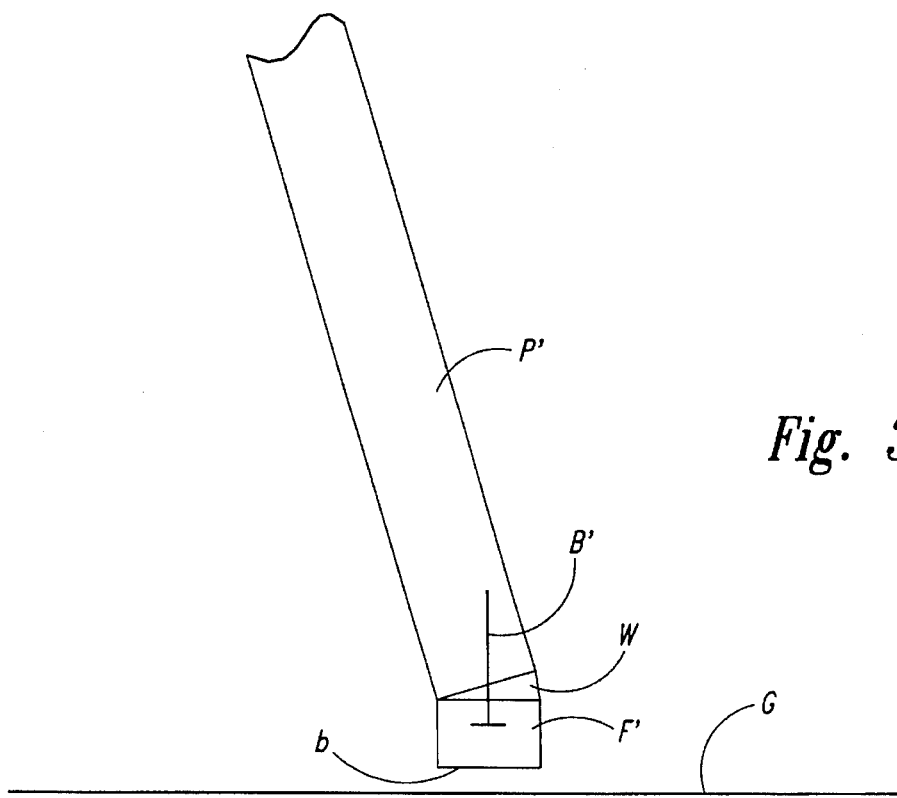
FIG. 3 is a side elevational view of a foot attached to the pylon of FIG. 2 in which an attempt is made to adjust the angle of the pylon/foot interface by placing a wedge between the foot and pylon.
Figure 4:
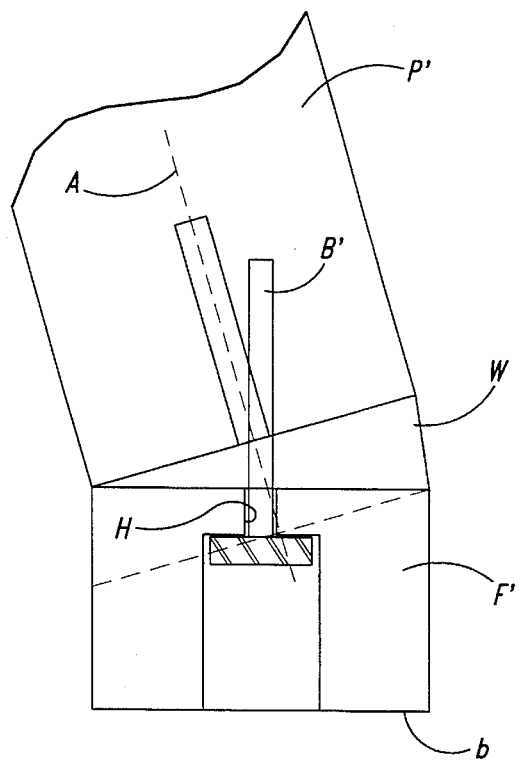
FIG. 4 is a schematic cross-section view of the pylon/foot interface of FIG. 3.

A solution to the problems caused by canted pylons might be to place a wedge W between the pylon P' and prosthetic foot F' as shown in FIG. 3. However, although the wedge W does make the bottom b of the prosthetic foot F' parallel to the ground G, an attachment bolt B' extending through the foot F' no longer extends along the axis of the pylon P' to engage threads of an axial bore A formed in the pylon P', as best shown in FIG. 4. If the angle of the bolt B' was altered so that the bolt B' was aligned with the axial bore A of the pylon P', the bolt B' could no longer extend along a bolt hole H formed in the prosthetic foot F'. As a result, it does not seem possible to use a wedge W to adjust the angle of the interface between fi conventional prosthetic foot and a pylon having an axial threaded bore for receiving an attachment bolt from the foot.

Figure 5A:
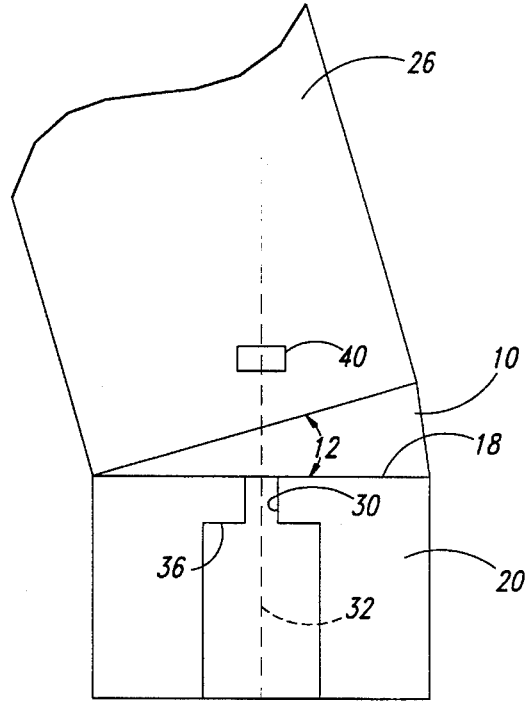
FIGS. 5A and B are schematic cross-section views of the inventive angular adjustment system for a pylon/foot interface illustrating its principle of operation.
Figure 5B:
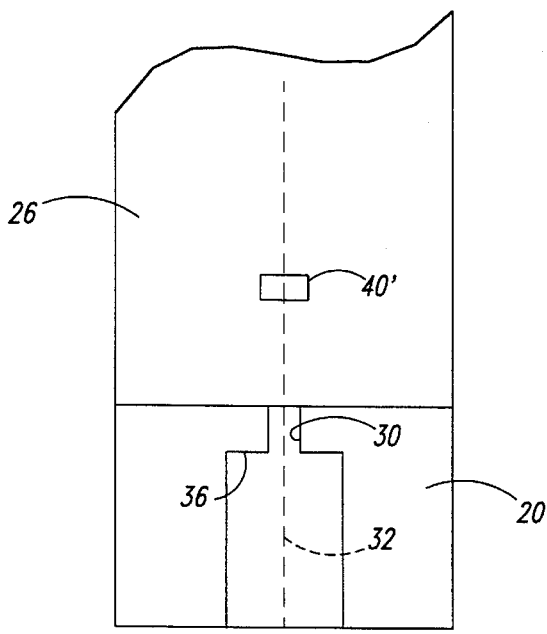

The inventive approach to solving the above-described problems and allowing a wedge to be positioned between a pylon and conventional prosthetic foot is illustrated in FIGS. 5A–B. As shown schematically in FIG. 5A, a wedge 10 having a wedge angle 12 is positioned between an upper mounting surface 18 of a prosthetic foot 20 and the lower end of a prosthetic pylon 26. A bolt hole 30, having a longitudinal axis 32 that extends into the pylon 26, is formed in the prosthetic foot 20. The lower end of the bolt hole 30 is surrounded by a bolt head surface 36.

The bolt hole 30 is adapted to receive a bolt (not shown in FIG. 5A) for securing the foot 20 to the pylon 26. The threaded shank of the bolt (not shown in FIG. 5A) engages a nut 40 that is mounted in the pylon 26. Without the prosthetic pylon 26 canted and the wedge 10 positioned between the upper mounting surface 18 and the lower end of prosthetic pylon 26, the threaded shank of the bolt engaged the nut 40' as shown in FIG. 5B. It will be apparent from FIGS. 5A–B that, if the prosthetic foot 20 is to remain centered in the medial/lateral plane under the wedge 10 once the wedge 10 is positioned and the prosthetic pylon 26 is canted, it is necessary for the position of the nut 40 to move relative to the pylon 26 in the medial/lateral plane. The nut 40 is therefore structured to move in the medial/lateral plane relative to the pylon 26. If the prosthetic foot 20 did not remain centered beneath the wedge 10, then the foot 20 would exert a torque on the pylon 26 in the same manner as described above with reference to FIG. 2.

Although an offset between the foot 20 and the pylon 26 in the medial/lateral plane is highly undesirable for the reason explained above, an offset in the anterior/posterior plane generally does not create significant problems. For this reason, the position of the nut 40 in the anterior/posterior plane generally need not be adjusted as the wedge 10 adjusts the angle of the interface between the foot 20 and pylon 26 in the anterior/posterior plane.

Figure 6:
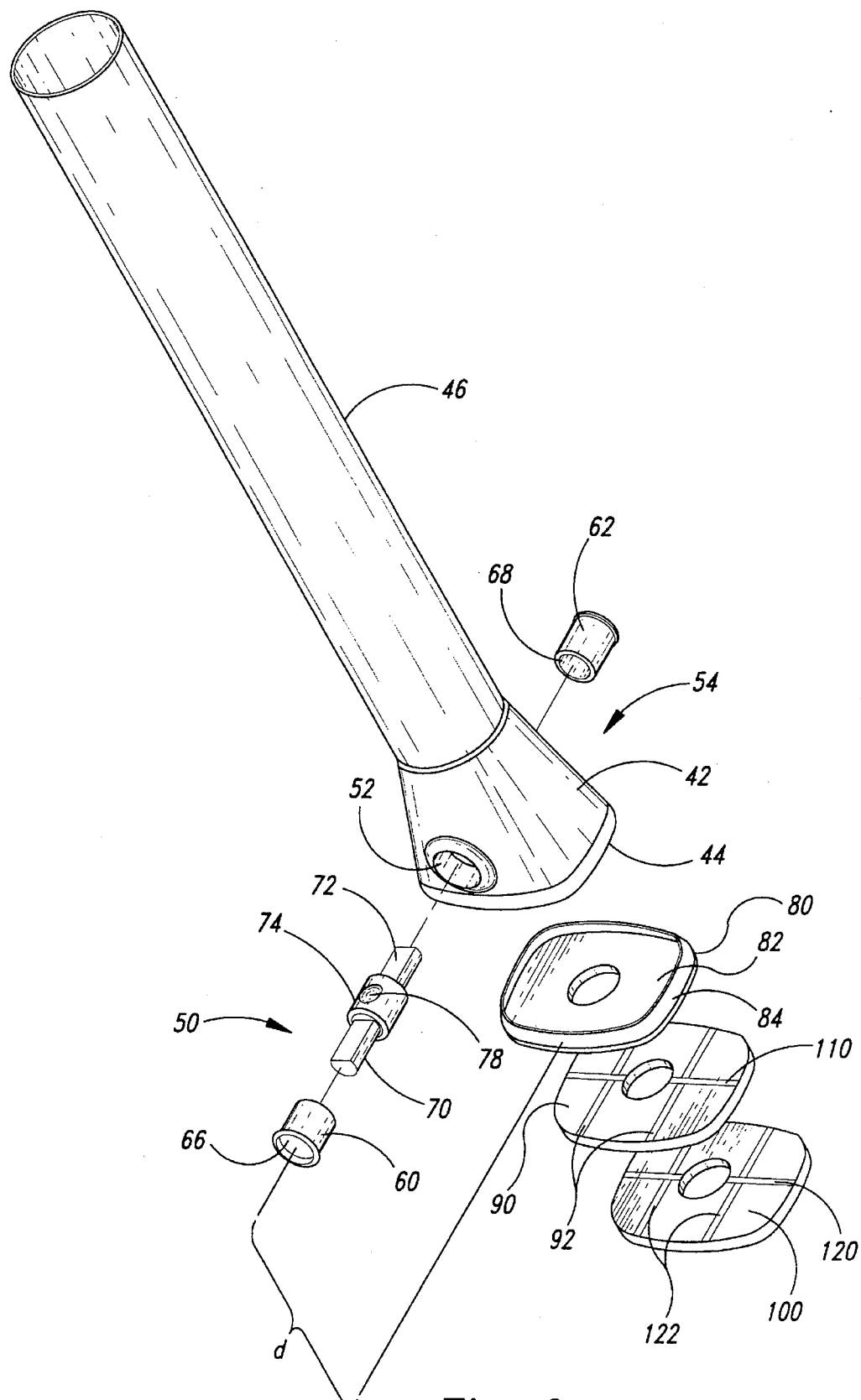
FIG. 6 is an exploded isometric view of a preferred embodiment of the inventive angular adjustment system for a pylon/foot interface

A preferred embodiment of a pylon 46 for allowing the interface between the pylon 46 and a prosthetic foot is illustrated in FIG. 6. The lower end 42 of the pylon 46 flares outwardly in all directions to create a relatively large prosthetic foot attachment surface 44. The pylon 46, including the flared lower end 42, is preferably tubular to create a hollow interior. A barrel nut assembly 50 is positioned inside the hollow interior of the flared lower end 42 for securing a prosthetic foot to the pylon 46 in an adjustable manner, as described in detail below.

A pair of cylindrical beating seats 52, 54 are formed in the flared lower end 42 diametrically opposite each other so that the seats 52, 54 are in axial alignment. The bearing seats 52, 54 receive respective cylindrical bearings 60, 62, one of which 60 is preferably thinner than the other 62. The bearings 60, 62 have formed therein respective cylindrical holes 66, 68 that are offset from the center of the bearings 60, 62. The holes 66, 68 receive respective axles 70, 72 extending in opposite directions from opposite end faces of a barrel nut member 74. A threaded bore 78 is formed in the barrel nut member 74 so that it extends perpendicular to the longitudinal axis of the barrel nut member 74. The bearings 60, 62, axles 70, 72 and barrel nut member 74 thus comprise the barrel nut assembly 50. As explained in detail below, the angle of the bore 78 in the anterior/posterior plane, as well as the position of the bore 78 relative to the pylon 46 in the medial/lateral plane, can be adjusted to adjust the angle between the pylon 46 and a prosthetic foot.

A preferred embodiment of the pylon 46 shown in FIG. 5, as illustrated in FIG. 6, includes an interface plate 80 having a planar member 82 surrounded by a low, upwardly facing wall 84. The interface plate 80 is positioned on the flared lower end 42 of the pylon 46 with the upper surface of the planar member 82 contacting the prosthetic foot attachment surface 44 and the wall 84 surrounding the outside of the lower end 42. The interface plate 80 is thus stationary in all directions with respect to the pylon 46. The planar member 82 can have a wedge angle in the medial/lateral plane so that the planar member 82 can be used to adjust for a cant of the pylon 46 in the medial/lateral plane, or the planar member 82 can be of a uniform thickness. A first wedge member 90 is positioned beneath the interface plate 80. The first wedge member 90 has a wedge angle in the anterior/posterior plane so that the first wedge member 90 can be used to adjust for a cant of the pylon 46 in the anterior/posterior plane. A second wedge member 100 is positioned beneath the first wedge member 90. The second wedge member 100 also has a wedge angle in the anterior/posterior plane so that the second wedge member 100 can also be used to adjust for a cant of the pylon 46 in the anterior/posterior plane. One or both of the first and second wedge members 90, 100, respectively, can be used in combination with the interface plate 80 having a planar member 82 with either a wedge angle or a uniform thickness to adjust for a cant of the pylon 46 in the medial/lateral plane, to adjust for a cant of the pylon 46 in the anterior/posterior plane, or to adjust for a cant of the pylon 46 in both planes. Also, several of either the first wedge member 90 or the second wedge member 100 can be used together to achieve wedge angles that are integer multiples of the wedge angle of a single wedge member 90, 100.

Although not apparent in FIG. 6, the lower surface of the planar member 82 has formed therein both a linear ridge extending in the anterior/posterior plane and a pair of parallel linear grooves extending in the medial/lateral plane. The linear ridge fits into a linear groove 110 formed in the upper surface of the first wedge member 90. The linear grooves formed in the lower surface of the planar member 82 fit onto parallel linear ridges 92 formed in the upper surface of the first wedge member 90. The interfit between the groove 110 and the linear ridge on the lower surface of the planar member 82, and between the linear ridges 92 and the linear grooves formed in the lower surface of the planar member 82 restrains relative movement between the wedge member 90 and the interface plate 80 in the medial/lateral direction, about the longitudinal axis of the pylon 46, and in the anterior/posterior direction.

Although also not apparent FIG. 6, the lower surface of the first wedge member 90 has formed therein both a linear ridge extending in the anterior/posterior plane and a pair of parallel linear grooves extending in the medial/lateral plane. The linear ridge formed in the lower surface of the first wedge member 90 fits into a linear groove 120 formed in the upper surface of the second wedge member 100. The linear grooves formed in the lower surface of the first wedge member 90 fit into parallel linear ridges 122 formed in the upper surface of the second wedge member 100. The interfit between all of these ridges and grooves prevents relative movement between the first wedge member 90 and the second wedge member 100 in the medial/lateral direction, about the longitudinal axis of the pylon 46, and in the anterior/posterior direction.

Although also not apparent FIG. 6, the lower surface of the second wedge member 100 has formed therein both a linear ridge extending in the anterior/posterior plane and a pair of parallel linear grooves extending in the medial/lateral plane. The linear ridge formed in the lower surface of the second wedge member 100 receives a linear groove (not shown) formed in the upper surface of an attachment surface of a conventional prosthetic foot known as the Seattle Foot® sold by Model and Instrument Development Corporation of Seattle, Wash. The interfit between the linear ridge formed on the lower surface of the second wedge member 100 and the linear groove (not shown) formed in the upper surface of the Seattle Foot® allows movement in the anterior/posterior plane. Thus, the prosthetic foot can move relative to the second wedge member 100 in the anterior/posterior direction, but cannot move relative to the second wedge member 100 in the medial/lateral direction or about the longitudinal axis of the pylon 46. Movement of the prosthetic foot relative to the second wedge member 100, and therefore relative to the cylindrical bearing seats 52, 54, in the anterior/posterior direction compensates for movement of the pylon 46, and therefore of the cylindrical bearing seats 52, 54, relative to the prosthetic foot in the anterior/posterior direction when the first and second wedge members 90 and 100 are positioned.

Of course, the grooves and notches on the lower surface of the planar member 82 can also mate to the corresponding notches and grooves on the upper surface of the second wedge member 100 or on the upper surface of the Seattle Foot®. Similarly, the grooves and notches on the lower surface of first wedge member 90 can also mate to the corresponding notches and grooves on the upper surface of the Seattle Foot®.

Figure 7A:
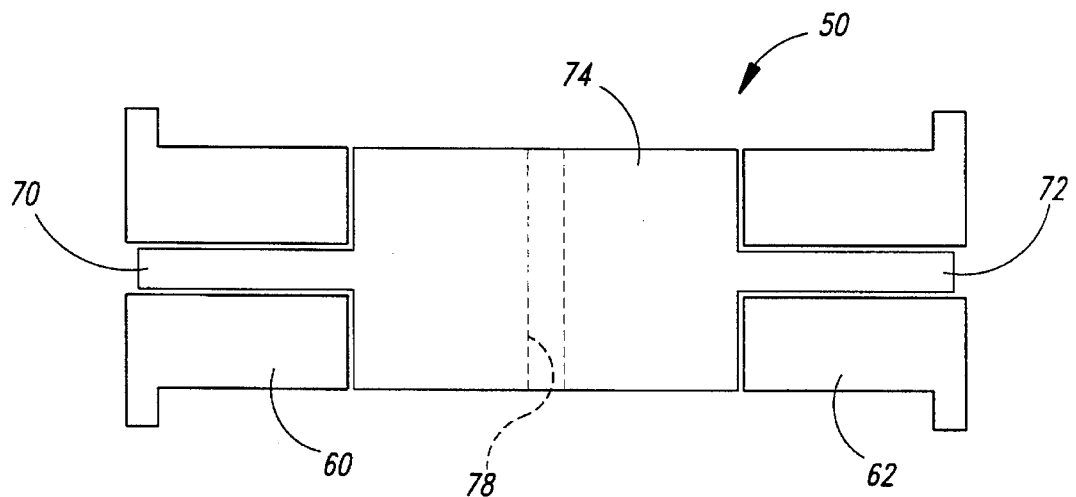
FIGS. 7A–C are cross-sectional views of a barrel nut assembly used in the angular adjustment system embodiment of FIG. 6.
Figure 7B:
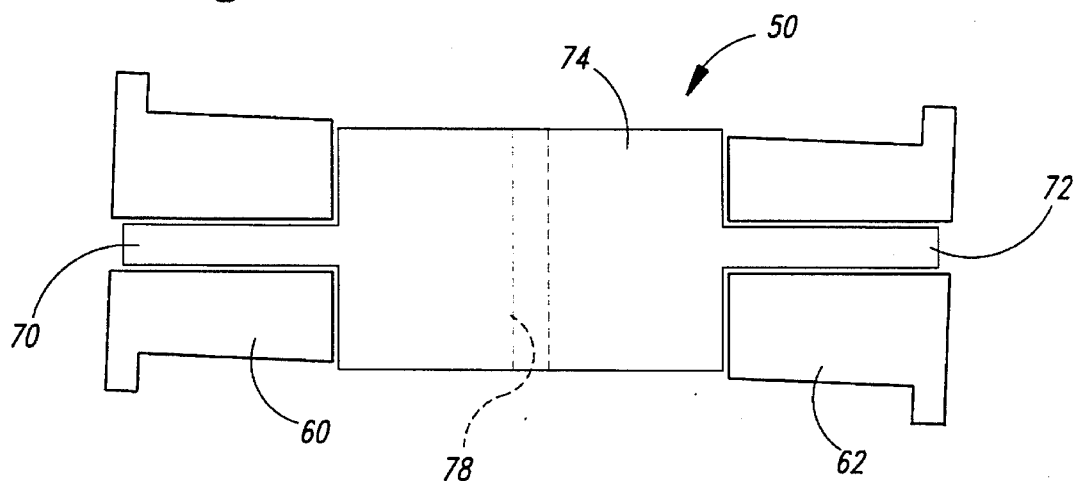
Figure 7C:
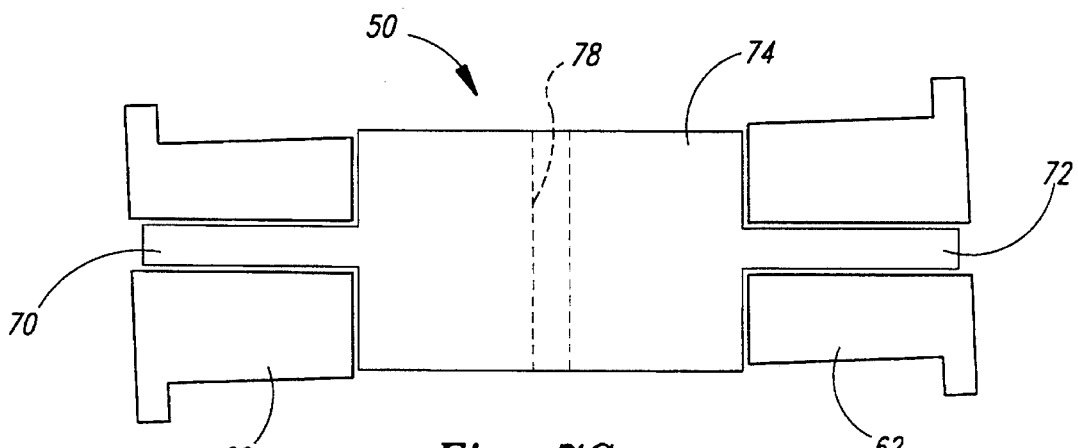

The manner in which the barrel nut assembly 50 allows the barrel nut member 74 to move in the medial/lateral plane and vary the angle of its threaded bore 78 in the anterior/posterior plane is best illustrated in FIGS. 7A–C. The barrel nut member 74 is shown in FIG. 7A with the barrel nut axles 70, 72 positioned at the same angular position with respect to their supporting bearings 60, 62, where neither of the beatings 60, 62 is thinner than the other. As a result of the position of the barrel nut axles 70, 72, the barrel nut member 74 is not tilted to either side so that the axis of the threaded bore 78 is vertical. However, by rotating the barrel nut axles 70, 72 in both of the bearings 60, 62, the angle of the threaded bore 78 in the anterior/posterior plane can be varied to accommodate the first and second wedge members 90 and 100 which have a wedge angle in the anterior/posterior plane.

When the bearings 60, 62 are rotated to opposite positions and the bearing 60 is made thinner than the bearing 62, as shown in FIG. 7B, one of the bearings 62 is offset downwardly while the other bearing 60 is offset upwardly. As a result, the threaded bore 78 is not angled in the medial/lateral plane while the pylon 46 is. Furthermore, since the thinner bearing 60 is positioned on the left and the wider bearing 62 is positioned on the right, the position of the threaded bore 78 is shifted to the left. Thus, when the barrel nut assembly 50 is in the position shown in FIG. 7B, it can accommodate the planar member 82 which can have a wedge angle in the medial/lateral plane.

When the positions of the barrel nut assembly 50 are reversed, as shown in FIG. 7C, the bearing 62 is offset upwardly while the bearing 60 is offset downwardly. As a result, the threaded bore 78 is not angled in the medial/lateral plane while the pylon 46 is. Furthermore, the position of the threaded bore 78 is shifted to the right to accommodate the planar member 82 having a wedge angle in the medial/lateral plane positioned in the opposite direction from its position in FIG. 7B.

In FIGS. 7B and 7C, the bearings 60 and 62 are formed to offset upwardly or downwardly at an angle equal to the planar member wedge angle if the planar member 82 is a distance d, as shown in FIG. 6, from the longitudinal axis of the barrel nut assembly 50. Thus, the planar member 82 should be positioned at this distance d from the longitudinal axis of the barrel nut assembly 50. Also, when the barrel nut assembly 50 is in either position shown in FIGS. 7B or C, the barrel nut member 74 may be rotated while keeping the bearings 60, 62 stationary to alter the angle of the threaded bore 78 in the anterior/posterior plane without affecting the position or angle of the threaded bore 78 in the medial/lateral plane.

Figure 8:
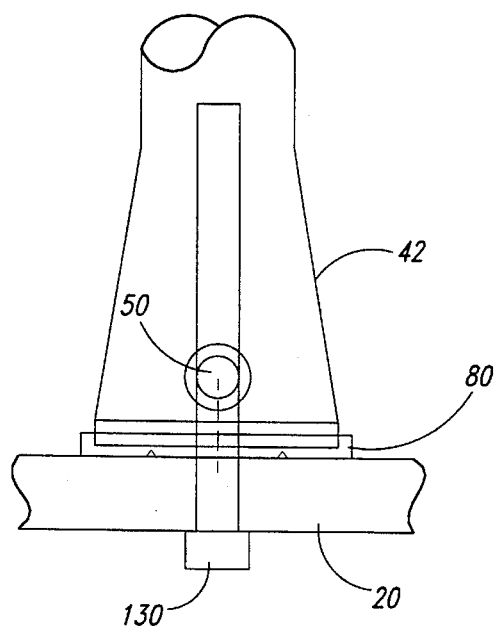
FIG. 8 is a schematic cross-section view showing the angular adjustment system embodiment of FIG. 6 without any angular adjustment.
Figure 9:
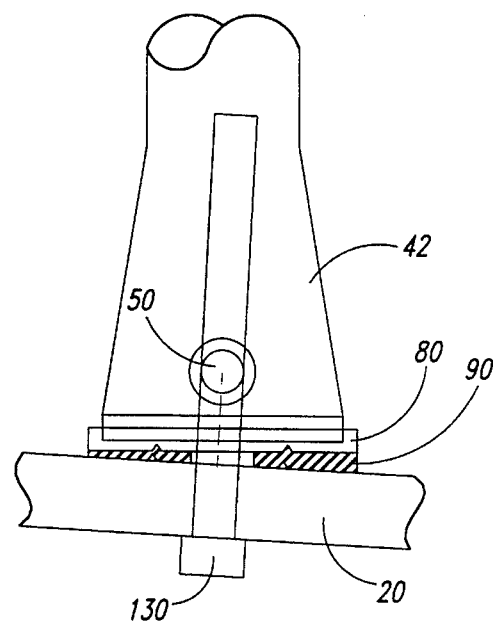
FIG. 9 is a schematic cross-section view showing the angular adjustment system embodiment of FIG. 6 with an angular adjustment in the anterior-posterior plane.
Figure 10:
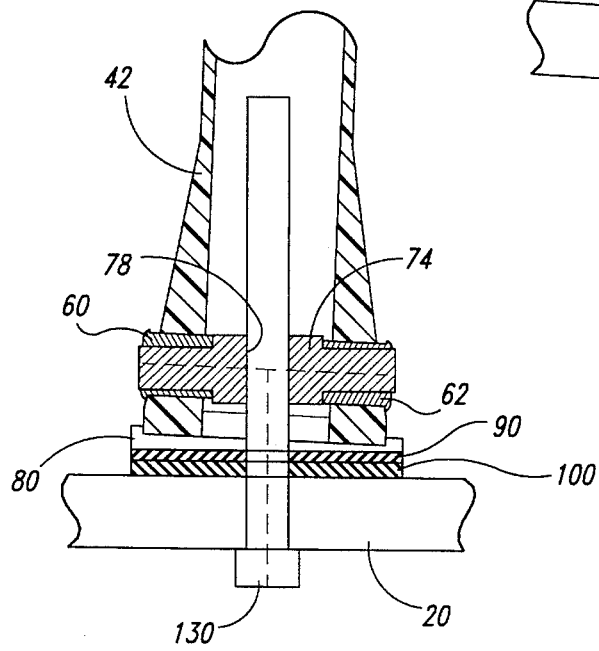
FIG. 10 is a schematic cross-section view showing the angular adjustment system embodiment of FIG. 6 with an angular adjustment in the medial-lateral plane.

The manner in which the various positions of the barrel nut assembly 50 can be used to accommodate the interface plate 80, having a planar member 82, and the wedge members 90 and 100 positioned between the pylon 46 and a prosthetic foot, is illustrated in FIGS. 8–10. With reference to FIG. 8, the interface plate 80 having a zero degree wedge angle is positioned on the lower end 42 of the pylon 46. An attachment bolt 130 extends vertically and is aligned with the longitudinal axis of the pylon 46. Thus, it is not necessary for the angle of the threaded bore 78 (FIGS. 6 and 7) to be adjusted in the anterior/posterior plane, nor is it necessary to adjust the position of the threaded bore 78 in the medial/lateral plane. For this reason, the barrel nut assembly 50 is placed in the position shown in FIG. 7A in which the barrel nut axles 70, 72 are positioned at the same angular position with respect to their supporting bearings 60, 62 and the barrel nut member 74 is not tilted to either side so that the axis of the threaded bore 78 is vertical.

The angular adjustment system is shown in FIG. 9 with the first wedge member 90 used to adjust the angular position of the interface between the pylon 46 and the prosthetic foot 20 to correct for a canting of the pylon 46 in the anterior/posterior plane. The barrel nut assembly 50 is placed in the position shown in FIG. 7A except that the barrel nut member 74 and the axles 70, 72 are rotated within the bearings 60, 62 to adjust the angle of the threaded bore 78 in the anterior/posterior plane so that the axis of the threaded bore 78 is aligned with the bolt 130. The prosthetic foot 20 has also moved to the left with respect to the lower end 42 of the pylon 46, the interface plate 80, and the first wedge member 90 so that the axis of the threaded bore 78 is aligned with the bolt 130.

The angular adjustment system is shown in FIG. 10 with the interface plate 80 having a wedge angle positioned on the lower end 42 of the pylon 46 used to adjust the angular position of the interface between the pylon 46 and the prosthetic foot 20 to correct for a canting of the pylon in the medial/lateral plane. The barrel nut assembly 50 is placed in the position shown in FIG. 7B to tilt the bearings 60, 62 in the medial/lateral plane. The thinner bearing 60 is also located at the left side of the pylon so that the barrel nut member 74 is offset to the left. As a result, the threaded bore 78 is aligned with the bolt 130 extending from the prosthetic foot 20.

It is thus seen that the inventive angular adjustment system allows conventional prosthetic feet to be safely and comfortably used with pylons that are canted in either the medial/lateral plane, the anterior/posterior plane, or both planes. From the foregoing, it will be appreciated that, although embodiments of the invention have been described herein for purposes of illustration, various modifications may be made without deviating from the spirit and scope of the invention. Accordingly, the invention is not limited except as by the following claims.

I claim:

1. A system for adjusting the angle between an elongated pylon and a prosthetic foot, said prosthetic foot having a bottom, a pylon attachment surface that is generally parallel to said bottom and is adapted to abut the lower end of said pylon, and a bolt hole extending through said pylon attachment surface, said bolt hole being surrounded by a bolt head surface that is parallel to said pylon attachment surface so that when said prosthetic foot is fastening to said pylon with a bolt extending through said hole into said pylon, a bolt head of said bolt rests against said bolt head surface, said system comprising:

a wedge having a pair of wedge surfaces intersecting each other at a wedge angle, said wedge being positioned between said pylon attachment surface and said pylon so as to impart a cant to said pylon, said wedge having a bolt hole extending therethrough in alignment with the bolt hole through said pylon attachment surface; and a generally cylindrical barrel nut assembly mounted in said pylon adjacent the lower end thereof, said assembly including:

a cylindrical barrel nut member having a threaded bore extending therethrough adapted to receive said bolt;

a pair of axles extending in opposite directions from opposite end faces of said cylindrical barrel nut member along the axis of said cylindrical barrel nut member; and a pair of cylindrical bearings each slidably engaging one of said axles with the centers of said bearings being radially offset in opposite directions from the axis of said cylindrical barrel nut member, said bearings being supported in said pylon at the lower end thereof so that the radial position of said barrel nut member is such that the axis of said threaded bore of said barrel nut member intersects the bolt hole through said pylon attachment surface, said barrel nut member being rotatable in said bearings to vary the angle of the axis of said threaded bore so that said threaded bore axis angle corresponds to said wedge angle.

2. The adjusting system of claim 1 wherein said barrel nut assembly is angularly and radially movable in the anterior-posterior plane.

3. The adjusting system of claim 1 wherein said barrel nut assembly is angularly and radially movable in the medial-lateral plane.

4. The adjusting system of claim 3 wherein said barrel nut assembly is also angularly and radially movable in the anterior-posterior plane.

5. The adjusting system of claim 1 wherein the width of said bearings are different from each other so that the radial position of said threaded bore can be varied between two positions by altering which of the two bearings are located at one side of said pylon.

6. The adjusting system of claim 1 wherein said wedge includes an alignment structure that interfits with an alignment structure of said prosthetic foot to restrain movement of said prosthetic foot relative to said wedge in at least one direction.

7. The adjusting system of claim 6 wherein said alignment structures restrains movement of said prosthetic foot relative to said wedge in the medial/lateral plane.

* * * * *